United States Patent
Martin et al.

(10) Patent No.: US 8,646,447 B2
(45) Date of Patent: Feb. 11, 2014

(54) SYSTEMS, METHODS, AND/OR APPARATUSES FOR NON-INVASIVE MONITORING OF RESPIRATORY PARAMETERS IN SLEEP DISORDERED BREATHING

(75) Inventors: Dion Charles Chewe Martin, Concord (AU); John David Oates, Castle Hill (AU)

(73) Assignee: ResMed Limited, Bella Vista (AU)

(*) Notice: Subject to any disclaimer, the term of this patent is extended or adjusted under 35 U.S.C. 154(b) by 1287 days.

(21) Appl. No.: 12/514,696

(22) PCT Filed: Nov. 13, 2007

(86) PCT No.: PCT/AU2007/001744
§ 371 (c)(1),
(2), (4) Date: May 13, 2009

(87) PCT Pub. No.: WO2008/058328
PCT Pub. Date: May 22, 2008

(65) Prior Publication Data
US 2010/0016694 A1    Jan. 21, 2010

Related U.S. Application Data

(60) Provisional application No. 60/858,414, filed on Nov. 13, 2006.

(51) Int. Cl.
| | |
|---|---|
| A62B 7/04 | (2006.01) |
| A61M 16/00 | (2006.01) |
| A62B 7/00 | (2006.01) |
| A61B 5/08 | (2006.01) |
| F16K 31/02 | (2006.01) |
| F16K 31/26 | (2006.01) |
| A61B 5/02 | (2006.01) |

(52) U.S. Cl.
USPC ............ 128/204.23; 128/204.18; 128/204.26; 600/538; 600/534; 600/484

(58) Field of Classification Search
USPC ........... 128/204.23, 204.18, 204.26; 600/323, 600/509, 538, 534, 484
See application file for complete search history.

(56) References Cited

U.S. PATENT DOCUMENTS

| 5,245,995 A | 9/1993 | Sullivan et al. |
| 5,682,877 A * | 11/1997 | Mondry .................. 128/204.23 |

(Continued)

FOREIGN PATENT DOCUMENTS

| JP | 2011131085 A * | 7/2011 |
| WO | WO 03/000125 | 1/2003 |

(Continued)

OTHER PUBLICATIONS

Hartert, T. V. "Use of Pulse Oximetry to Recognize Severity of Airflow Obstruction in Obstructive Airway Disease: Correlation With Pulsus Paradoxus." Chest 115.2 (1999): 475-81. Print.*

(Continued)

*Primary Examiner* — Oren Ginsberg
*Assistant Examiner* — Sundhara Ganesan
(74) *Attorney, Agent, or Firm* — Nixon and Vanderhye, PC

(57) ABSTRACT

In certain example embodiments, an air delivery system includes a controllable flow generator operable to generate a supply of pressurized breathable gas to be provided to a patient for treatment and a pulse oximeter. In certain example embodiments, the pulse oximeter is configured to determine, for example, a measure of patient effort during a treatment period and provide a patient effort signal for input to control operation of the flow generator. Oximeter plethysmogram data may be used, for example, to determine estimated breath phase; sleep structure information; autonomic improvement in response to therapy; information relating to relative breathing effort, breathing frequency, and/or breathing phase; vasoconstrictive response, etc. Such data may be useful in diagnostic systems.

5 Claims, 10 Drawing Sheets

(56) References Cited

U.S. PATENT DOCUMENTS

| | | | |
|---|---|---|---|
| 5,704,345 | A | 1/1998 | Berthon-Jones |
| 6,091,973 | A | 7/2000 | Colla et al. |
| 6,325,761 | B1 | 12/2001 | Jay |
| 6,363,270 | B1 | 3/2002 | Colla et al. |
| 6,445,942 | B1 | 9/2002 | Berthon-Jones |
| 6,484,719 | B1 * | 11/2002 | Berthon-Jones ......... 128/204.23 |
| 6,512,938 | B2 * | 1/2003 | Claure et al. .................. 600/323 |
| 6,648,828 | B2 * | 11/2003 | Friedman et al. ............. 600/506 |
| 6,675,797 | B1 * | 1/2004 | Berthon-Jones ......... 128/204.23 |
| 6,702,752 | B2 * | 3/2004 | Dekker ........................ 600/484 |
| 6,920,877 | B2 | 7/2005 | Remmers et al. |
| 6,988,994 | B2 | 1/2006 | Rapoport et al. |
| 7,004,908 | B2 | 2/2006 | Sullivan et al. |
| 7,035,679 | B2 * | 4/2006 | Addison et al. ............... 600/323 |
| 7,081,095 | B2 * | 7/2006 | Lynn et al. .................... 600/538 |
| 7,740,591 | B1 * | 6/2010 | Starr et al. .................... 600/534 |
| 2003/0036689 | A1 * | 2/2003 | Diab et al. .................... 600/323 |
| 2003/0100843 | A1 * | 5/2003 | Hoffman ....................... 600/538 |
| 2004/0040560 | A1 * | 3/2004 | Euliano et al. ........... 128/204.23 |
| 2005/0061319 | A1 | 3/2005 | Hartley et al. |
| 2005/0070774 | A1 * | 3/2005 | Addison et al. ............... 600/323 |
| 2005/0081855 | A1 * | 4/2005 | Berthon-Jones ......... 128/204.23 |
| 2005/0143672 | A1 * | 6/2005 | Green et al. .................. 600/529 |
| 2005/0217674 | A1 * | 10/2005 | Burton et al. ............. 128/204.23 |
| 2007/0032733 | A1 * | 2/2007 | Burton .......................... 600/509 |
| 2008/0066753 | A1 * | 3/2008 | Martin et al. ............. 128/204.23 |
| 2011/0192400 | A9 * | 8/2011 | Burton et al. ............. 128/204.23 |

FOREIGN PATENT DOCUMENTS

| | | |
|---|---|---|
| WO | WO 2004/075746 | 9/2004 |
| WO | WO 2006/037184 | 4/2006 |

OTHER PUBLICATIONS

International Search Report for PCT/AU2007/001744, mailed Jan. 22, 2008.

Written Opinion for PCT/AU2007/001744, mailed Jan. 22, 2008.

* cited by examiner

SYSTEMS, METHODS, AND/OR APPARATUSES FOR NON-INVASIVE MONITORING OF RESPIRATORY PARAMETERS IN SLEEP DISORDERED BREATHING

CROSS-REFERENCES TO RELATED APPLICATIONS

This application claims the benefit of PCT Application No. PCT/AU2007/001744, filed on Nov. 13, 2007, and U.S. Provisional Application No. 60/858,414, filed on Nov. 13, 2006, the entire contents of each of which are hereby incorporated herein in its entirety. This application further incorporates by reference the entire contents of each of PCT Application No. WO 2006/037184, filed on Oct. 6, 2005, and U.S. Provisional Application No. 60/615,961, filed on Oct. 6, 2004.

FIELD OF THE INVENTION

The invention relates to monitoring parameters relevant to Sleep Disordered Breathing (SDB).

BACKGROUND OF THE INVENTION

Sleep Disordered Breathing (SDB) has been traditionally identified as being associated with Obstructive Sleep Apnea (OSA) and Cheyne-Stokes Respiration (CSR). Today there are a number of other conditions also recognized as being associated with SDB including, e.g., cardiovascular disease, stroke and diabetes, etc. Patients with these conditions and SDB may benefit from the treatment of their SDB with positive pressure ventilatory support by some form of mechanical ventilator.

While basic nasal Continuous Positive Airway Pressure (CPAP) ventilators may not monitor their patients, in general, the patients benefit from having a device which monitors the patients as part of some kind of control loop. In particular devices are known to monitor pressure, flow and patient effort.

An existing problem for known devices includes discriminating between obstructive sleep apnea (OSA) and central sleep apnea (CSA). OSA is indicative of upper airway collapse and can be used as an input to auto-titration algorithms for the CPAP pressure applied or the end-expiratory pressure (EEP) used in a bi-level device. CSA can be indicative of over-ventilation and can therefore be used as an input to algorithms that auto-titrate the ventilation of the patient. Clearly, miscategorizing an apnea as either closed or open results in these titration algorithms prescribing sub-optimal parameters for the treatment of the patient.

Obstructive and central sleep apnea are discriminated in known devices by injecting a 1 cm peak-to-peak 4 Hz oscillation into the treatment pressure waveshape and measuring the resulting 4 Hz flow. The general term for this technique is Forced Oscillation Technique (FOT). The phasic difference in the flow to the pressure waveshape is indicative of the compliance of the load which is then used to deduce if the upper airway is opened or closed. Unfortunately, this method does not give any information on events that include upper airway narrowing/closure and simultaneous central sleep apnea.

Obstructive and central sleep apnea are also discriminated in known devices by detecting the cardiogenic flow. The cardiogenic flow is the airflow induced in the lungs during a heart beat due to the proximity of the lungs to the heart. During OSA, there is therefore never any cardiogenic flow. Like the previous solution, it is also unable to determine if CSA and OSA have occurred concurrently.

Another existing problem for known devices includes inferring high patient respiratory effort. Patient respiratory effort is a key indicator used by clinicians when evaluating the acute state of a patient in a number of diseases including sleep apnea, obstructive lung disease, and various restrictive diseases. Despite its known value, it has not enjoyed widespread use as either an input to flow generator titration algorithms or as a recorded clinical parameter due to the inconvenience or impracticality of the transducers involved.

The "gold standard" in terms of accuracy for monitoring effort is an oesophageal catheter which a patient is required to swallow. Unfortunately, this is uncomfortable and awkward for a patient and not practical outside a clinic. Respiratory bands around the patient's chest and abdomen are known to monitor effort. Suprasternal notch effort sensors are also known, as well as the use of EMG and ECG sensors. These techniques are all unsuitable for home use.

Another existing problem for known devices includes measuring and storing vaso-specific parameters, such as cardiac afterload, vascular tone, heart rate variability, sympathetic nervous system activity in general, and/or central venous pressure. If these parameters were available in real-time in a flow generator, they could be used to (a) contribute to auto-titration algorithms and (b) be recorded with respiratory specific parameters to allow physicians to observe long-term trends and have a richer data set to determine the long term management of the patient.

Yet another existing problem for known devices includes limiting the mean mask pressure. Auto-titrating CPAP algorithms aimed at eliminating OSA or upper airway resistance syndrome (UARS) may use breath flow analysis to limit upper airway narrowing. Pressure beyond certain levels may, in some patients, be deleterious to cardiac function. Equally, a lower pressure may be beneficial to cardiac function provided it does not result in complete closure of the upper airway (e.g., a lower pressure may promote UA closure). It is desirable to include cardiovascular parameters in auto-titration schemes such that respiratory therapy (e.g., CPAP pressure) can be continuously optimized. Such parameters may include cardiac afterload, vascular tone, heart rate variability, sympathetic nervous system activity in general, and/or central venous pressure if they could be acquired non-invasively and conveniently.

ResMed's AutoSet CS and AutoSet CS2 devices specifically target patients with heart disease. These devices address the 'excessive CPAP pressure' problem by imposing a maximum average pressure of 15 cm $H_2O$.

Another known sensor is a suprasternal notch effort sensor. See U.S. Pat. No. 6,445,942 (Berthon-Jones). Other known techniques for monitoring apneas and hypopneas are described in U.S. Pat. Nos. 6,091,973 (Colla et al.) and 6,363,270 (Colla et al.). Another related U.S. patent is U.S. Pat. No. 5,704,345 (Berthon-Jones) which describes distinguishing open and closed airway apneas amongst other things. U.S. Pat. No. 6,484,719 (Berthon-Jones) describes a servo-ventilator which uses a flow sensor. The contents of all these patents are hereby expressly incorporated by reference herein.

Thus, a need has developed in the art to overcome one or more of these and other disadvantages.

SUMMARY OF THE INVENTION

One aspect of the present invention relates to therapy through ventilator optimization through one or more of improving synchrony, pressure support/volume autotitration, reducing side-effects (e.g., excessive EEP); and patient management (such as, for example, trending respiration, cardiac/autonomic function, sleep structure, endothelial function, etc.).

Another aspect of the present invention relates to therapy through CPAP optimization, including one or more of OSA/CSA discrimination, reducing side-effects (e.g., excessive EEP), auto-titration, and patient management (such as, for example, trending cardiac/autonomic function, sleep structure, endothelial function, etc).

Still another aspect of the present invention relates to monitoring and/or diagnosis. SDB diagnosis and patient management may be achieved via oximetry alone or in combination with respiratory flow (apnealink). SDB diagnosis may includes both OSA and CSA.

Yet another aspect of the present invention relates to monitoring and/or diagnosis via early detection of exacerbations in respiratory disease (e.g., trending).

An aspect of the present invention relates to monitoring and/or diagnosis by monitoring of autonomic function, sleep quality, respiratory timing/effort, and vascular tone (e.g., arterial stiffness) in general (including, for example, patient sub-groups such as cardiac failure, stroke, hypertension, pediatrics, obesity-hypoventilation syndrome, motor-neurone disease, etc.).

It will be appreciated that in any of the above, the PPG information may stand alone, or be combined/correlated with respiratory flow or traditional $SpO_2$ from the oximeter or with other respiratory monitors such as trans-cutaneous $CO_2$. It also will be appreciated that the techniques for monitoring, detection, and treatment may be used alone or in any combination.

Certain example embodiments provide for an air delivery system, comprising a controllable flow generator operable to generate a supply of pressurized breathable gas to be provided to a patient for treatment; a pulse oximeter configured to generate, during a treatment period, a patient effort signal for input to control operation of the flow generator; and a controller configured to derive an estimated breath phase of the patient independent of measured flow, based at least in part on the patient effort signal.

In certain example embodiments, a method for treating sleep disordered breathing is provided, with the method comprising deriving a pulse oximeter signal from a patient; processing the pulse oximeter signal to generate a patient effort signal indicative of respiratory rate; and deriving an estimated breath phase of the patient independent of measured flow based at least in part on the patient effort signal.

In still other example embodiments, a respiratory effort monitoring apparatus is provided, comprising a pulse oximeter configured to derive a pulse oximeter signal; and a signal processor configured to receive the pulse oximeter signal and generate signals indicative of respiratory effort. The apparatus can be used in conjunction with a method for diagnosing SDB, respiratory disease (including asthma), and/or cardiac failure (e.g., periodic breathing). The signal processor may be configured to derive an estimated breath phase of the patient independent of measured flow based at least in part from the patient effort signal.

In other example embodiments, an air delivery system comprises a controllable flow generator operable to generate a supply of pressurized breathable gas to be provided to a patient for treatment; a pulse oximeter; and a controller configured to determine sleep structure information for the patient is tracked to indicate a therapy's effectiveness based at least in part on output from the pulse oximeter.

Still other certain example embodiments provide a method for diagnosing sleep disordered breathing, with that method comprising deriving a pulse oximeter signal from a patient; processing the pulse oximeter signal to generate a patient effort signal indicative of respiratory rate; and tracking sleep structure information for the patient to indicate a therapy's effectiveness.

Certain example embodiments provide a respiratory effort monitoring apparatus, comprising a pulse oximeter configured to derive a pulse oximeter signal; and a signal processor configured to receive the pulse oximeter signal and generate a patient effort signal indicative of respiratory rate; wherein the signal processor is configured to track sleep structure information for the patient to indicate a therapy's effectiveness.

Certain other example embodiments provide an air delivery system, comprising a controllable flow generator operable to generate a supply of pressurized breathable gas to be provided to a patient for treatment; a pulse oximeter configured to determine a measure of patient effort during a treatment period and provide a patient effort signal for input to control operation of the flow generator; and a controller configured to extract information regarding patient-ventilator asynchrony from the patient effort signal, and to measure and/or monitor the patient's autonomic improvement in response to therapy.

Still other example embodiments provide a method for monitoring cardio-respiratory data associated with sleep disordered breathing, with the method comprising deriving a pulse oximeter signal from a patient; processing the pulse oximeter signal to generate a patient effort signal indicative of respiratory rate; measuring and/or monitoring the patient's autonomic improvement in response to therapy; and extracting patient-ventilator asynchrony from the patient effort signal.

In certain example embodiments, a respiratory effort monitoring apparatus is provided, comprising a controllable flow generator operable to generate a supply of pressurized breathable gas to be provided to a patient for treatment; a pulse oximeter configured to determine a measure of patient effort during a treatment period and provide a patient effort signal for input to control operation of the flow generator; and a controller to extract patient-ventilator asynchrony from the patient effort signal, and to measure and/or monitor the patient's autonomic improvement in response to therapy.

In certain other example embodiments, an air delivery system for clinical management and/or prediction of respiratory exacerbations is provided, comprising a controllable flow generator operable to generate a supply of pressurized breathable gas to be provided to a patient for treatment; and a pulse oximeter; wherein the controllable flow generator and/or the pulse oximeter are configured to determine information relating to relative breathing effort, breathing frequency, and/or breathing phase.

In still other example embodiments, a method for clinical management and/or prediction of respiratory exacerbations is provided, the method comprising deriving a pulse oximeter signal from a patient; and processing the pulse oximeter signal to determine information relating to relative breathing effort, breathing frequency, and/or breathing phase, with or without standard oximeter metrics such as oxygen saturation and average heart-rate.

Yet other example embodiments provide a respiratory effort monitoring apparatus for clinical management and/or prediction of respiratory exacerbations comprising a controllable flow generator operable to generate a supply of pressurized breathable gas to be provided to a patient for treatment;

and a pulse oximeter; wherein the controllable flow generator and/or the pulse oximeter are configured to determine information relating to relative breathing effort, breathing frequency, and/or breathing phase.

Certain example embodiments provide an air delivery system with provision for assessment of endothelial dysfunction comprising a controllable flow generator operable to generate a supply of pressurized breathable gas to be provided to a patient for treatment; a pulse oximeter configured to measure the patient's vasoconstrictive response to treatment; and a controller configured to trend the vasoconstrictive response over a given time period to indicate a change in endothelial function.

Still other example embodiments provide a method for assessment of endothelial dysfunction, the method comprising deriving a pulse oximeter signal from a patient; processing the pulse oximeter to measure the patient's vasoconstrictive response to treatment; and trending the vasoconstrictive response over a given time period to indicate a change in endothelial function.

Certain other example embodiments provide a method of monitoring sleep-disordered breathing, the method comprising deriving a pulse oximeter signal from a patient; processing the pulse oximeter signal to generate a patient effort signal indicative of respiratory rate; measuring saturation variation; and, correlating the patient effort signal with the saturation variation to detect and/or quantify the level of periodic breathing by the patient.

Parameters of interest (e.g., cardiac afterload, vascular tone, heart rate variability, and/or central venous pressure, etc.) can be estimated from a pulse oximeter plethysmograph. Currently, pulse oximeters are primarily employed for monitoring $SpO_2$ and heart-rate. Some pulse oximeters display a plethysmograph, but as far as is known, none of the information present in the plethysmograph is used as input to auto-titrate respiratory or cardiovascular therapies. Peripheral Arterial Tone (PAT) is a novel multi-cell finger plethysmography system that focuses specifically on arterial tone. This technology may be an alternative to pulse oximetry as the sensing modality. Pulse-transit time (PTT) also contains information on autonomic activity and arterial tone.

Each aspect can be manifested in the form of a method and/or apparatus for non-invasive monitoring of one or more parameters relating to the diagnosis of a patient's health disorder, e.g., sleep disordered breathing, congestive heart failure, stroke, respiratory disease, etc., and/or controlling a ventilator or other respiratory therapy device in accordance with the monitored parameter and/or the derived diagnosis.

Another aspect of the invention is to monitor a patient using pulse oximeter plethysmography without treating them.

Further aspects of the invention are set out in the attached claims.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF EMBODIMENTS

Figure 1:
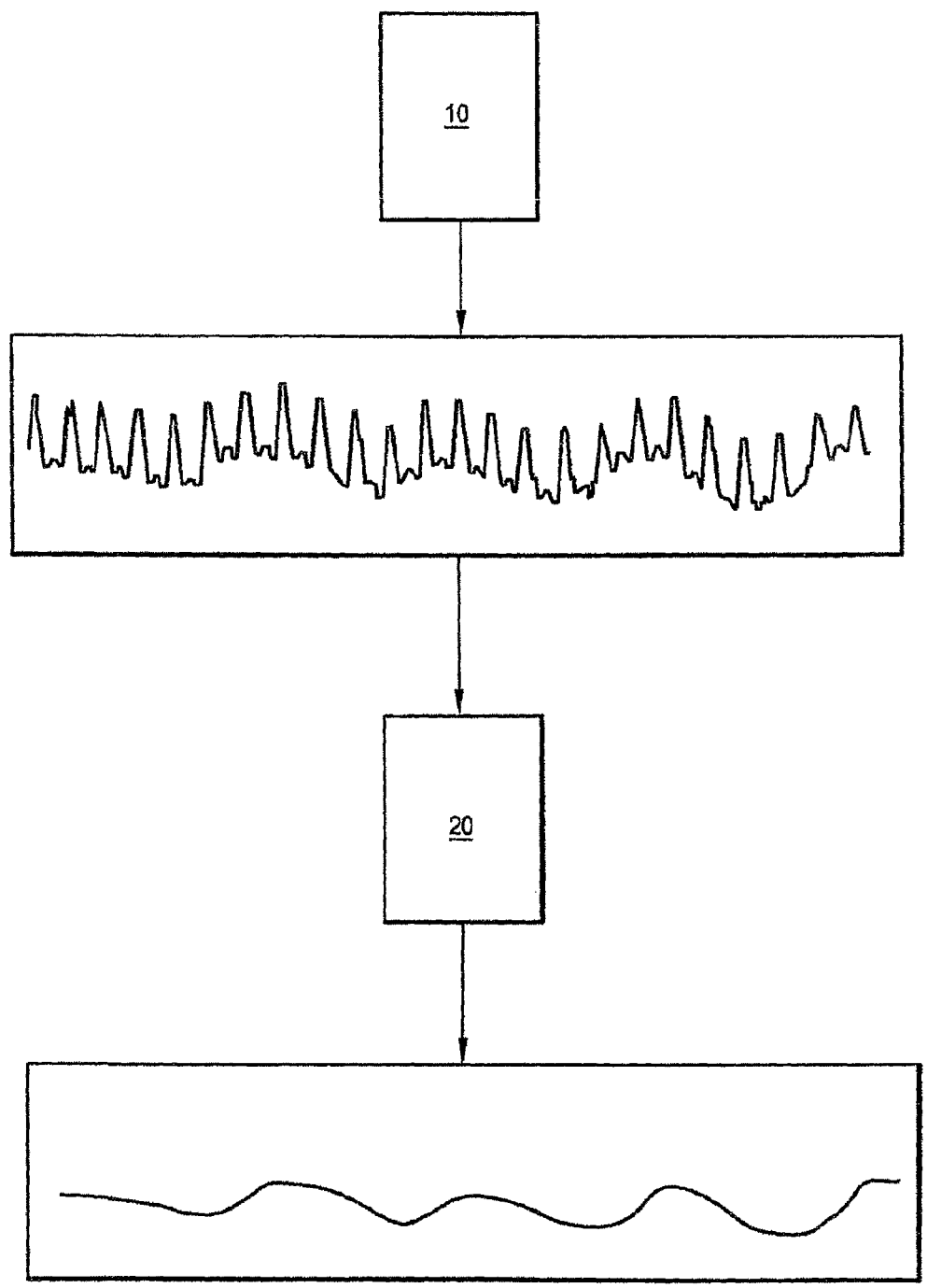
FIG. 1 shows a pulse oximeter waveform transformed into an effort signal.

Pulse oximeter plethysmography (sometimes referred to simply as "pulse oximetry" or "photo-plethysmogram" (PPG)) is a standard method of obtaining blood oxygenation data in a non-invasive and continuous manner. Oximeters use two wavelengths of light to solve for hemoglobin saturation. The waveforms are created by the absorption produced by pulsatile arterial blood volume, which represents the alternating current (AC) signal. The absorption produced by nonpulsatile blood, venous and capillary blood, and tissue absorption is depicted by the direct current (DC) signal. See Hartert et al., *Use of Pulse Oximetry to Recognize Severity of Airflow Obstruction in Obstructive Airway Disease, Correlation with Pulsus Paradoxus*, Chest 1999:115:475-481. A pulse oximeter signal from Hartert et al. is shown in FIG. 1.

Currently, pulse oximeters are primarily employed for monitoring $SpO_2$ and heart-rate; however, in accordance with an embodiment of the invention, the pulse oximeter is used as an indication of patient effort in a respiratory therapy device. Respiratory effort can be seen in the arterial blood pressure waveform as variation in the peak-to-peak amplitude. This is caused by the effect of the respiratory pleural pressure swings on cardiac output throughout the breathing cycle. Inspiration is associated with reduced systolic blood pressure, and this respiratory effect on blood pressure is referred to as 'pulsus paradoxus.'

This effect has been proposed as a measure of respiratory loading in various areas (e.g., asthma exacerbation, obstructive lung disease, etc.), where a variation of >10 mmHg is associated with high respiratory effort. The reference standard for measuring arterial blood pressure is invasive (catheter), so indirect methods are desired. One such method is pulse-transit time (PTT), where the variation in blood pressure causes a variation in vascular compliance, transduced as the propagation time of the pulse from the heart to the periphery. Another method is the oximeter plethysmographic waveform, which relates the volume of arterial blood in the tissue bed being sensed (usually finger or ear). Changes in cardiac output throughout the respiratory cycle may be seen as variation in the plethysmogram's peak-to-peak amplitude, consistent with the arterial blood pressure observations. This variation in cardiac output, combined with the variation in central venous pressure due to respiration, also induces changes in the baseline/offset of the PPG signal synchronous with breathing. A third factor seen in the PPG is affected by breathing: the heart period is also modulated somewhat by respiration, primarily via the respiratory neural outflow, and to a lesser extent in response to the arterial pressure variations induced by respiration.

Since the pulse oximeter plethysmogram is more related to volume of blood in the tissues, variation in the baseline/offset of the pulsatile component may be a more sensitive indicator of cardiopulmonary interaction than the cardiac output variation (Hartert et al., Use of Pulse Oximetry to Recognize Severity of Airflow Obstruction in Obstructive Airway Disease—Correlation with Pulsus Paradoxis; Chest 1999; 115: 475-481).

Other factors (e.g., arterial tone, cardiac performance, postural changes, etc.) can also cause variations in the PPG, so processing is required to analyze the variation over the respiratory frequencies, and can be aided further by correlating the variation with respiratory flow information provided by the flow generator. A progressive increase in PPpleth (pulsus paradoxus from the plethysmogram) over a number of breaths (e.g., 3-5) may indicate increasing efforts associated with impending upper airway (UA) collapse. A dramatic increase in PPpleth might indicate UA obstruction.

The waveform may be characterised into the following categories:

(a) Pulsatile amplitude: The AC amplitude of the pulse is most indicative of vascular compliance, which is greatly affected by arterial tone/sympathetic nervous system activity when looked at over 20-30 seconds or greater (for an example of methods, refer Am J Physiol Heart Circ Physiol 283; H434-H439, 2002). As such, it can indicate arousal from apnea, and over many days/weeks, may demonstrate the long-term benefits of abolishing OSA/UARS on SNS activity. The finger is the best site for detecting the effect of autonomic activity on vascular compliance. Pulse oximetry at the ear is less sensitive to autonomic activity, but can offer a relative estimate of central blood pressure, given that vascular compliance exerts a lesser effect.

(b) Offset or baseline: Respiration induces a phasic variation in the pulse baseline (pulsus paradoxus) that varies in accordance with respiratory effort (the pressor response). This effect has been used to identify airway resistance (asthma) and obstruction (obstructive lung disease). See Comparison of traditional and plethysmographic methods for measuring pulsus paradoxus (Clark J et al., Arch Pediatr Adolesc Med 2004. 158: 48-51) and use of pulse oximetry to recognize severity of airflow obstruction in obstructive airway disease; correlation with pulsus paradoxus (Hartert et al., Chest 1999. 115: 475-481. Available online at http://www.chestjournal.org/cgi/reprint/115/2/475).

(c) Pulse rhythm/timing: Pulse timing and heart period can shed light on numerous physiological factors, dealt with in turn below.

Sympatho-vagal balance: Heart-rate variability indices (HRV, traditionally derived from ECG signals) can be calculated from the pulse period, inferring sympatho-vagal balance as performed routinely in ECG analysis (for an overview, see Circulation 1996; 93: 1043-1065).

Sleep structure: Statistical or fractal analysis of pulse interval data throughout a night can distinguish sleep-wake state. REM sleep is similar to wake periods in the fractal component of HRV/heart period, but the non-REM sleep stages differ significantly from awake (see http://www.ncbi.nlm.nih.gov/entrez/query.fcgi?cmd=Retrieve&db=pubmed&dopt=Abstract &list_uids=12059594; http://ajpheart.physiology.org/cgi/reprint/280/1/H17; http://ajpheart.physiology.org/cgi/reprint/283/1/H434). HRV data might be analyzed to indicate sleep onset, since the patient must pass through non-REM sleep prior to achieving REM sleep. Heart-rate can be obtained via various monitors (e.g., ECG, standard oximeter, etc.). The PPG inherently contains heart period, and provided this period information is not averaged, it can be used to conduct traditional HRV analyses. Thus, the PPG signal provides the opportunity to capture unfiltered heart-rate data, in contrast to typical pulse oximeter heart-rate outputs. One method of discriminating sleep/wake from HRV is taught by Ivanov et al., Europhysics Letters 1999, 48(5): 594-6000.

Vascular tone and sympathetic activation: Simultaneous access to an ECG signal in addition to the oximeter pulse timing can offer an indication of vascular tone, which can augment the sensitivity or specificity of any conclusions regarding arousal, respiratory effort, or sympathetic tone. The ECG can indicate the moment of electrical systole, so the time delay between this central cardiac timing and the arrival of the pulse at the periphery can define the left-ventricle's pre-ejection period plus the transit time of the pulse through the systemic arteries to the peripheral probe site. This overall duration is the traditional definition of pulse-transit time, or PTT. Pulse transit time is affected by vascular tone (also referred to as arterial stiffness), which can be affected by factors such as sympathetic activation and blood pressure. Consequently PTT can be an indicator of arousal (transient increases in sympathetic outflow and BP) and an indicator of average BP/average sympathetic activation when viewed over longer periods. An alternate means of calculating pulse-transit time is to replace the timing of electrical systole with mechanical systole, e.g., cardiogenic flow (CGF) seen in a respiratory flow signal (e.g., acquired during ventilator or CPAP therapy or using a nasal pressure transducer), after deducting a fixed propagation delay from lung to nares. By combining the timing of the cardiogenic respiratory flow signal with the timing of the plethysmographic pulse it may be possible to calculate relative variations in pulse-transit time more accurately than traditional PTT (pulse transmission time) estimates, since the left-ventricle's pre-ejection period is not included in the measured duration (the pre-ejection period is known to sometimes detract from the sensitivity of the ECG-derived PTT measurement). In addition, by acquiring the CGF pulse at a consistent place within the respiratory cycle (end expiration, when it is most readily seen), the respiratory-induced fluctuations in PTT can be ignored. That leaves just the PTT variations due to either BP variation or changes in arterial tone (sympathetic activation), both of which shorten the PTT, and both of which are associated with arousal, thereby offering another important SDB parameter. For an overview of PTT methods and applications, refer to Thorax 1999; 54: 452-458.

(d) Waveshape: The wave morphology contains similar information to that seen in arterial catheter pressure signals or applanation tonometry. Some examples include:

Vascular tone: For example, the position and relative amplitude of the "dicrotich notch" (e.g., the bump on the trailing shoulder of the pleth waveform) can point to the degree and timing of pressure-wave reflections of the forward-going wave from the peripheral circulation, and may be itself an indicator of vasomotor tone (SNS). This feature can be trended using established methods: for example, the first-derivative of the plethysmogram is closely related to arterial flow to the area, while the second-derivative of the waveform has been proposed as an indicator of vasoactivity and arterial compliance (e.g., Hypertension 1998; 32: 365-370).

Cardiac congestion/impeded venous return: Venous pulsation may be apparent in the waveform, which represents interaction between a number of factors, but in our case may indicate the effect of excessive CPAP (increased central venous pressure) or improvement in congestive heart failure (reduced central venous pressure). Certain examples of venous pulsation within the PPG waveform are illustrated in chapter 23 of Clinical Monitoring: Practical applications for anesthesia and critical care, WB Saunders & Co, 2001.

Methods for extracting the above parameters from the raw PPG exist, comprising, for example, time-domain or frequency-domain signal processing techniques, or elements of both. One example are the methods taught in WO 03/00125 A1 and WO 2004/075746 A2, employing the continuous wavelet transform to extract the respiratory signals and arterial tone information from the raw PPG. Time-domain analysis of assessing baseline fluctuations from the PPG are summarized by Shamir et al, British Journal of Anaesthesia 1999, 82(2): 178-81

Recent developments in oximeter signal processing has allowed device performance to be more robust when presented with movement and low perfusion. Modern embedded processors allow more sophisticated post-processing of plethysmographic waveforms, and even the most advanced oximeter technology is available as OEM module format. These technological advances, together with the underlying information present in the plethysmogram combined with information from the therapy device, may permit a respiratory device to employ an oximeter as part of a servo-controlled therapy.

The information present in the plethysmogram may be useful to diagnosis-only studies as well, since it can indicate arousals that may not be evident as a desaturation.

Respiratory effects can also be seen as variation in cardiac timing, termed 'respiratory sinus arrhythmia,' which may also be used to extract respiratory timing information.

An aspect of the invention relates to the combination of (1) oximeter plethysmograph-derived parameters with (2) respiratory flow information, to augment real-time control algorithms for a respiratory therapy device.

This arrangement may prove superior to current techniques if, for example, it permits a more thorough and timely estimate of the patient's acute condition allowing algorithms to prescribe more appropriate therapy. The parameters are also optionally stored within the flow generator to give a physician a richer data set for long term patient management. This is superior to current technologies as it gives a physician data from flow generators used in an unsupervised environment similar to that gained in a sleep study.

Plethysmographic parameters useful for titration and long term patient management include all those noted above (e.g., patient effort, vascular compliance, heart rate variability, arrhythmia detection, venous pulsation, and SpO2, etc.).

In accordance with an embodiment of the invention, a pulse oximeter signal 10 is fed through signal processor 20, for example, a low pass filter, peak detection, nadir detection or averaging. The filter is designed to remove signals indicative of heart rate and leave signals indicative of respiratory rate.

Figure 2:
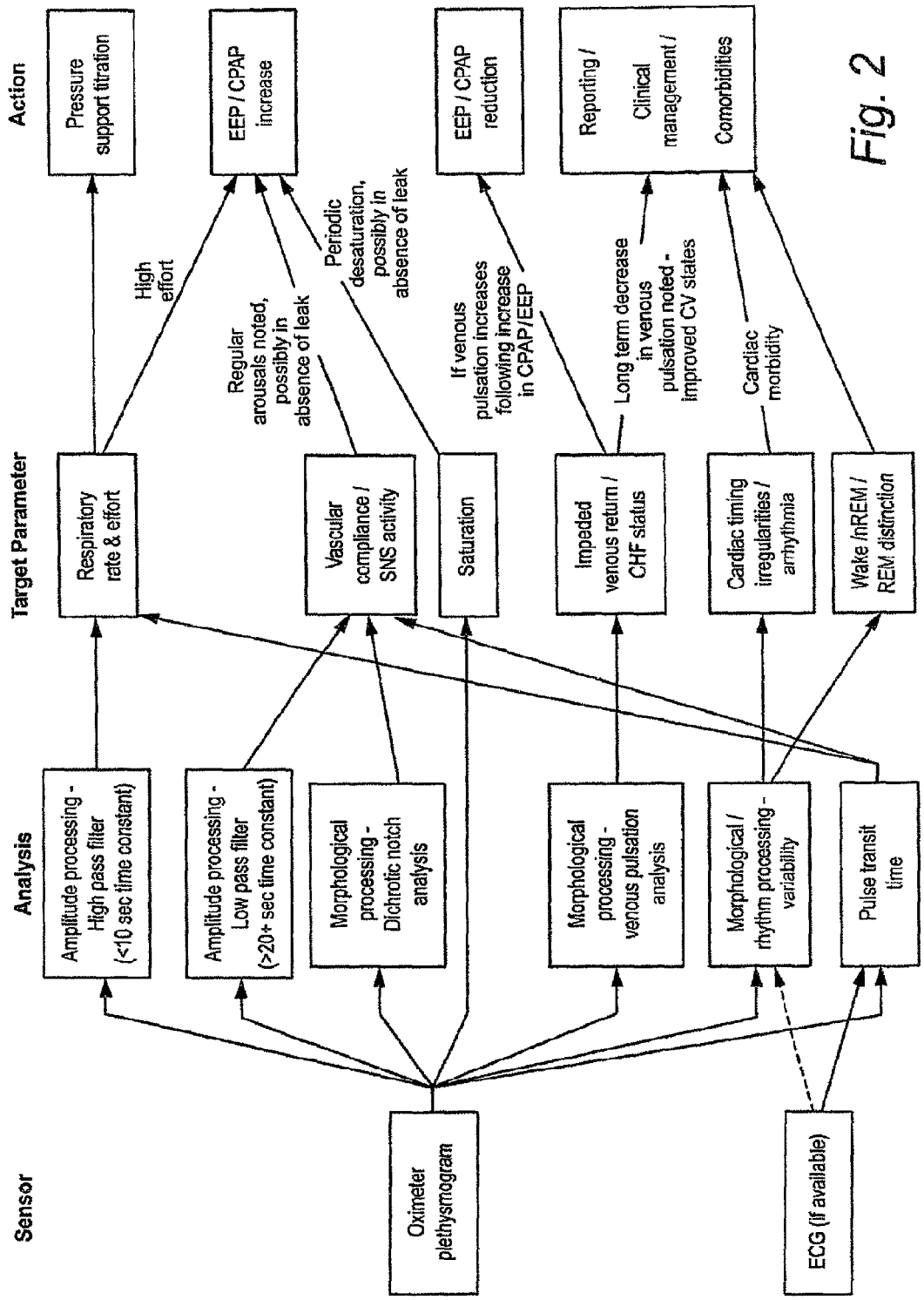
FIG. 2 shows a range of pulse oximetry applications in accordance with various embodiments of the invention.

Once the raw PPG signal is acquired from the pulse oximeter, it may be analyzed in a number of ways as shown in FIG. 2 and described in further detail below:

(i) Open-Closed Apnea Discrimination. The plethysmographically derived respiratory effort estimate can be used during episodes of apnea (using respiratory flow data) to indicate whether the apnea is opened (non-obstructed) or closed (obstructed), useful in automatic titration algorithm logic. For example, a low or zero flow signal is indicative of an apnea. If the apnea occurs in the absence of effort as measured by the pulse oximeter (e.g., no change or reduction in the relative effort signal), then the apnea is regarded as being "open." However, if there is effort (e.g., increase in the relative effort signal), then the apnea is regarded as being "closed."

(ii) High airway resistance. Similarly, a period of high respiratory effort derived from the oximeter plethysmograph (e.g., increase in the relative effort signal) combined with unchanged or reduced respiratory flow, or combined with flow limitation (inferred by flow waveshape, as taught, for example, in U.S. Pat. Nos. 5,704,345, 6,920,877, and 6,988,994, each of which is incorporated herein by reference in its entirety) can imply the presence of significant airway resistance, be it due to expiratory flow limitation or upper-airway resistance. In both cases, the combination of high relative effort with unchanged or low measured respiratory flow may be an indicator to increase applied PEEP.

(iii) Relative work of breathing: In the absence of respiratory flow limitation (adjudged from respiratory flow waveshape or estimated volumes), persistently high respiratory effort may indicate inadequate pressure support (under-ventilation).

(iv) Used in conjunction with a flow based measure of phase (such as described in U.S. Pat. No. 6,484,719, which is incorporated herein by reference in its entirety).

(v) Using the relative effort information to augment ResMed's AutoSet CPAP algorithm. Increasing patient effort (e.g., increase in relative effort over 3-5 breaths) is indicative of impending upper-airway instability. AutoCPAP titration based on increased patient effort may be more pre-emptive of obstruction than the current flattening based algorithm.

(vi) Using the effort information as a basis for an algorithm in a ResMed's VPAP or AutoCS device to titrate applied PEEP. It is conceivable that titration algorithms based on inspiratory waveshape will be challenged when used in devices that change the pressure during the breath cycle. Changes in patient effort may not be as dependent on intra-breath changes in pressure and hence may be more robust to these types of therapy.

(vii) Using the relative effort signal as an early indicator that a patient has been overventilated. This may be a possible consequence of inappropriate servo-ventilation, where a ventilator augments the patient's ventilation to achieve a target level. This indicator can be used to titrate the target ventilation.

In addition, by offering an alternate estimate of breath phase independent of measured flow, spontaneous breath phase may be more accurately assessed, permitting, for example:

Indication of patient-ventilator asynchrony, useful for acute ventilatory configuration, for assisting clinical management of chronically ventilated patients, etc.

Predictive breath-phase algorithms improving synchrony, particularly in conditions such as obstructive lung disease where inspiratory flow is not an accurate indicator of the start of inspiratory effort.

(viii) Using venous pulsation as an input to ResMed's AUTOSET CPAP algorithms for patients with OSA and heart failure. Increases in venous pulsation can be used to limit the CPAP pressure applied to safer limits.

(ix) Using vascular compliance as an input to ResMed's CPAP algorithms. Changes in vascular compliance can be indicative of patient arousals. This can be used to augment the data currently used for automatically prescribing CPAP levels.

(x) Comparison of the respiratory effort estimate with the respiratory device's own estimate of breath phase (parameter used in ResMed's AutoCS2 and AutoVPAP) may allow a more robust breath-tracking scheme within the respiratory device; for example, it may improve leak rejection or leak estimation.

(xi) Sleep state—inference of sleep structure, sleep onset and sleep termination.

Analysis of the plethysmographic waveshape, possibly in combination with other monitored variables, may be used to optimize CPAP or VPAP therapies to reduce arterial stiffness, independently associated with poor cardiovascular prognosis. For example:

(i) Calculation and trending of pulse-transit time (method outlined in above). Accurate PTT estimation may offer additional information to that of the plethysmograph alone, contributing to the estimation of arterial tone/SNS activity and/or respiratory effort, and allowing closed-loop therapies aiming to optimise arterial compliance.

(ii) The morphology of the plethysmographic waveform may offer information directly associated with vascular compliance, for example, the position of the so-called 'diochrotic notch' relative to the initial systolic peak, allowing closed-loop therapies aiming to optimise arterial compliance.

With reference to FIG. 3-7 it is noted that:

THERAPY ALGORITHM adjustments may include:
Level of PEEP/CPAP
Level of Pressure support Concerning the two feedback signals F/B1 and F/B2 it is noted that:

F/B1 (Airflow-inferred patient parameter) may include any or all of the following:
Minute ventilation estimate
Inspiratory airflow limitation (e.g., UA flattening index)
Expiratory airflow limitation (e.g., expiratory flow waveform morphology)
Tidal volume
Leak
Cardiac timing (time of systolic ejection, extracted from cardiogenic flow)
Respiratory phase F/B 2 (PPG-inferred patient parameter) may include any or all of the following:
Relative indication of respiratory effort (e.g., high effort leads to increased respiratory baseline variation of PPG, pulsus paradoxus)
Absolute indication of respiratory rate
Patterns of respiratory effort and rate indicative of respiratory control anomalies or apnea type (crescendo/decrescendo in breathing effort, statistical derivations from respiratory patterns)
Indication of respiratory rate (e.g., variation of PPG amplitude and timing parameters)
Relative indication of worsening cardiac function (e.g., cardiac decompensation results in increased respiratory baseline variation of PPG, pulsus paradoxus)
Relative indication of venous congestion (e.g., degree of venous pulsation in PPG-morphological analysis)
Relative variation in sympathetic nervous system activity or arterial compliance (e.g., variation of PPG pulse amplitude over >20-30 second timescale, or shift in location of dicrotic notch)

Figure 3:
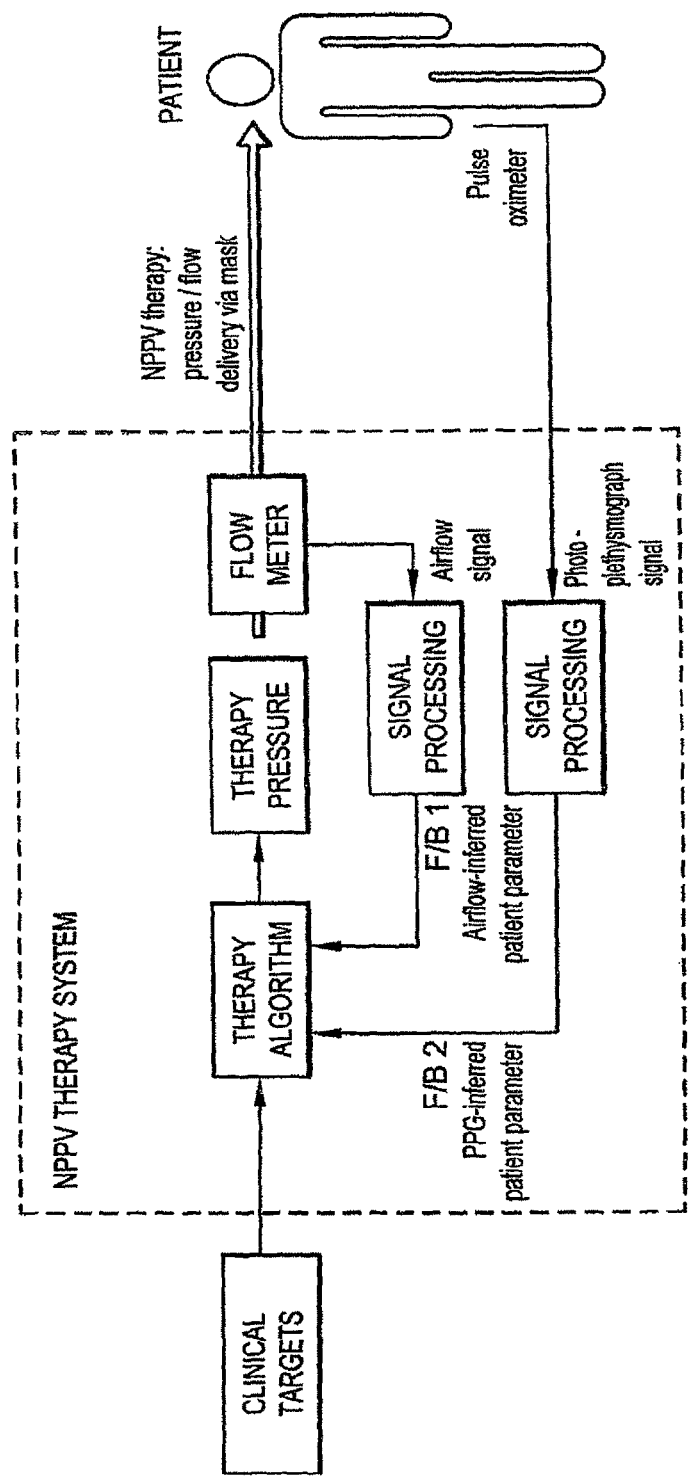
FIG. 3 shows a therapy system in accordance with an embodiment of the invention.
Figure 3A:
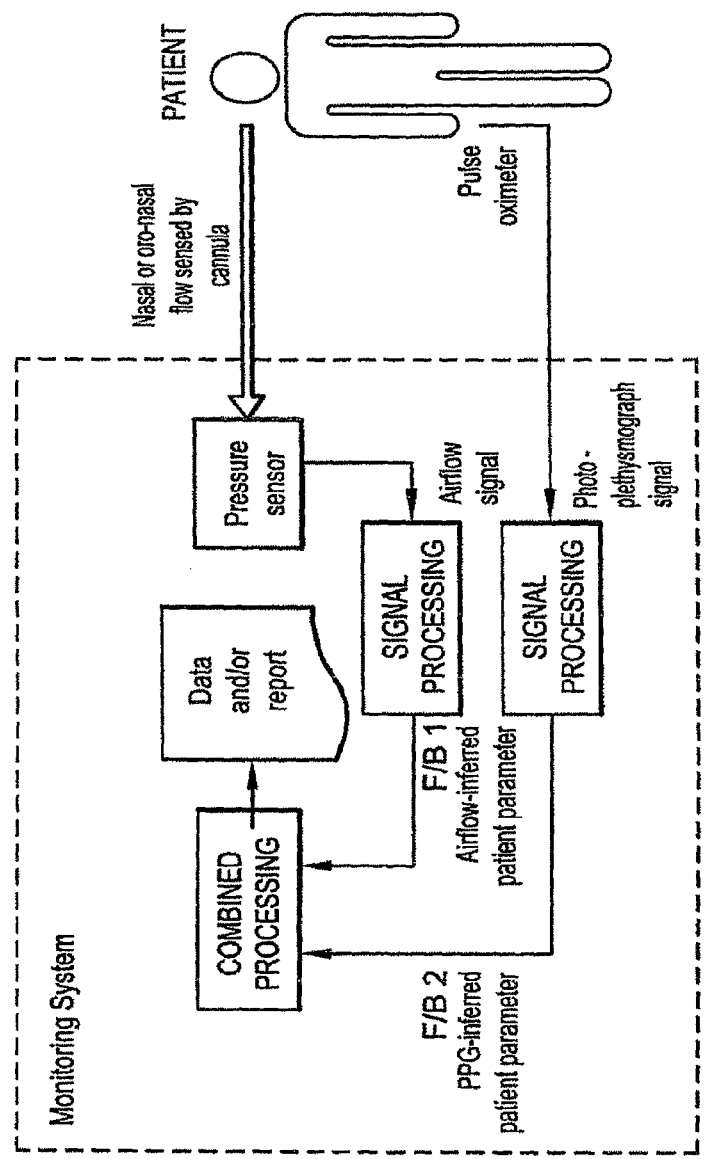
FIG. 3A is a schematic diagram of a monitoring system according to an embodiment of the present invention.

Standard pulse oximetry ($SpO_2$)
Arrival time of systolic pulse at periphery (e.g., systolic rise in PPG).
Pulse rate CLINICAL TARGETS may include:
Minimum ventilation (e.g., Respiratory Insufficiency, Obesity Hypoventilation patients)
Nominal ventilation (e.g., Cheyne-Stokes Respiration patients
Optimal synchrony
Sleep quality (all patients)
Long-term cardiac function (e.g., CHF/CSR/hypertensive patients).
Anticipation/prediction of cardiac decompensation (e.g., CHF patients)
Optimal arterial compliance
Minimum CPAP/EEP/PEEP
Maximum CPAP/EEP/PEEP
Minimum Pressure Support
Maximum Pressure
Maximum Average Pressure FIG. 3A is a schematic diagram for a monitoring system according to an embodiment of the present invention. Concerning the feedback signals F/B1 and F/B2, and the "Combined Processing" box, it is noted that:

F/B1 (Airflow-inferred patient parameter) may include any or all of the following:
Inspiratory airflow limitation (e.g., UA flattening index)
Expiratory airflow limitation (e.g., expiratory flow waveform morphology)
Cardiac timing (time of systolic ejection, extracted from cardiogenic flow)
Respiratory phase
Time course of breath amplitude and derived statistics F/B 2 (PPG-inferred patient parameter) may include any or all of the following:
Relative indication of respiratory effort (e.g., high effort leads to increased respiratory baseline variation of PPG, pulsus paradoxus), trended over durations relevant to the application (any amount of time ranging from, for example, a number of breaths to a number of months).
Absolute indication of respiratory rate.
Relative indication of worsening cardiac function (e.g., cardiac decompensation results in increased respiratory baseline variation of PPG, pulsus paradoxus)
Relative indication of venous congestion (e.g., degree of venous pulsation in PPG-morphological analysis)
Relative variation in sympathetic nervous system activity or arterial compliance (e.g., variation of PPG pulse amplitude over >20-30 second timescale, or shift in location of dicrotic notch), as seen during arousal from sleep.
Standard pulse oximetry ($SpO_2$)
Arrival time of systolic pulse at periphery (e.g., systolic rise in PPG).
Pulse rate COMBINED PROCESSING may include:
F/B 2 alone with no combined processing (e.g., a single parameter derived from the oximeter signal).
Delay between respiration changes (F/B1) and blood gas adjustments (F/B 2), eg to infer circulatory delay.
Pulse transit time (PTT) indicated by delay between cardiogenic flow pulses (F/B1) and arrival of the pulse at the periphery (F/B 2).
Multiple parameters within F/B 2 alone (e.g., respiratory effort and oxygen saturation).

CLINICAL MONITORING TARGETS may include:
Assessment of SDB
Assessment of sleep quality (all patients)
Assessment of cardiac function (e.g., CHF/CSR/hypertensive patients) as an adjunct to patient management.
Early warning of exacerbation of respiratory compromise, as common in chronic obstructive pulmonary disease or asthma.

FIGS. 4-7 show a number of algorithms performing various embodiments of the invention. Embodiments of the invention may take the form of a method and/or apparatus to monitor, in a non-invasive manner, one or more parameters, e.g., pulse oximetry and/or air flow, relating, e.g., to a patient's breathing and/or heart activity.

The monitored parameter or parameters may be used for diagnostic purposes, e.g., to log data, to produce a report or an alarm or otherwise signal a physician. In addition, or in the alternative, the values of the monitored parameter(s) may be used to control, e.g., stop, start or vary, the delivery of pressurized gas (e.g., timing, flow pressure) from a blower, ventilator or the like, to the patient.

Figure 4:
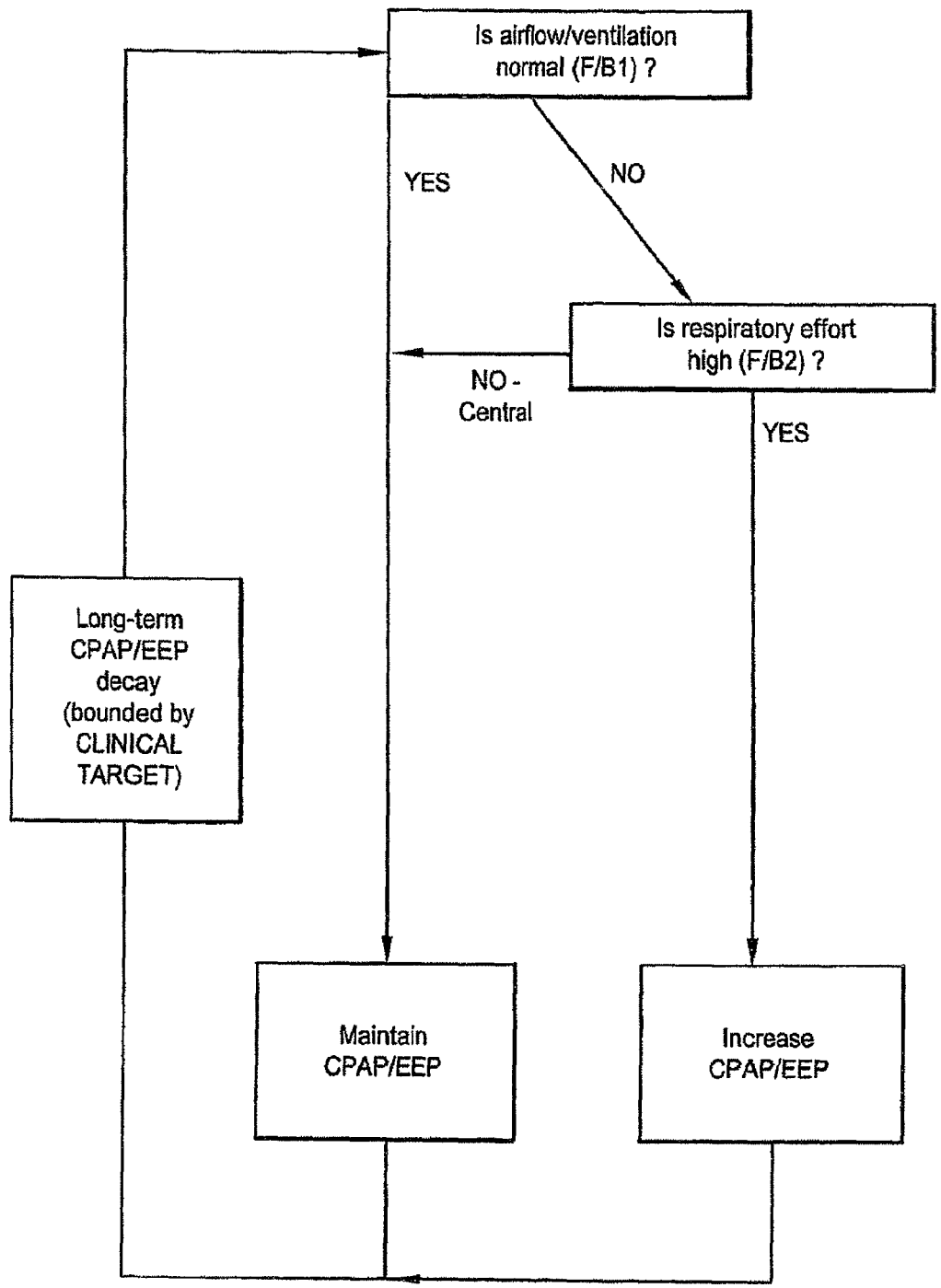
FIG. 4 shows an algorithm for Upper-airway obstruction (inspiratory flow limitation) and Auto-EEP/AutoCPAP in accordance with an embodiment of the invention.

FIG. 4 shows an open/closed airway apnea algorithm. An airflow signal is analyzed and a determination is made as to whether it is within normal bounds. If it is then CPAP/EPAP therapy is maintained at its current level. If the airflow signal is not normal, for example low indicative of an apnea, then the effort signal is analyzed. If the effort is high then an obstructive apnea may be indicated and the appropriate therapy is to increase the treatment pressure.

Figure 5:
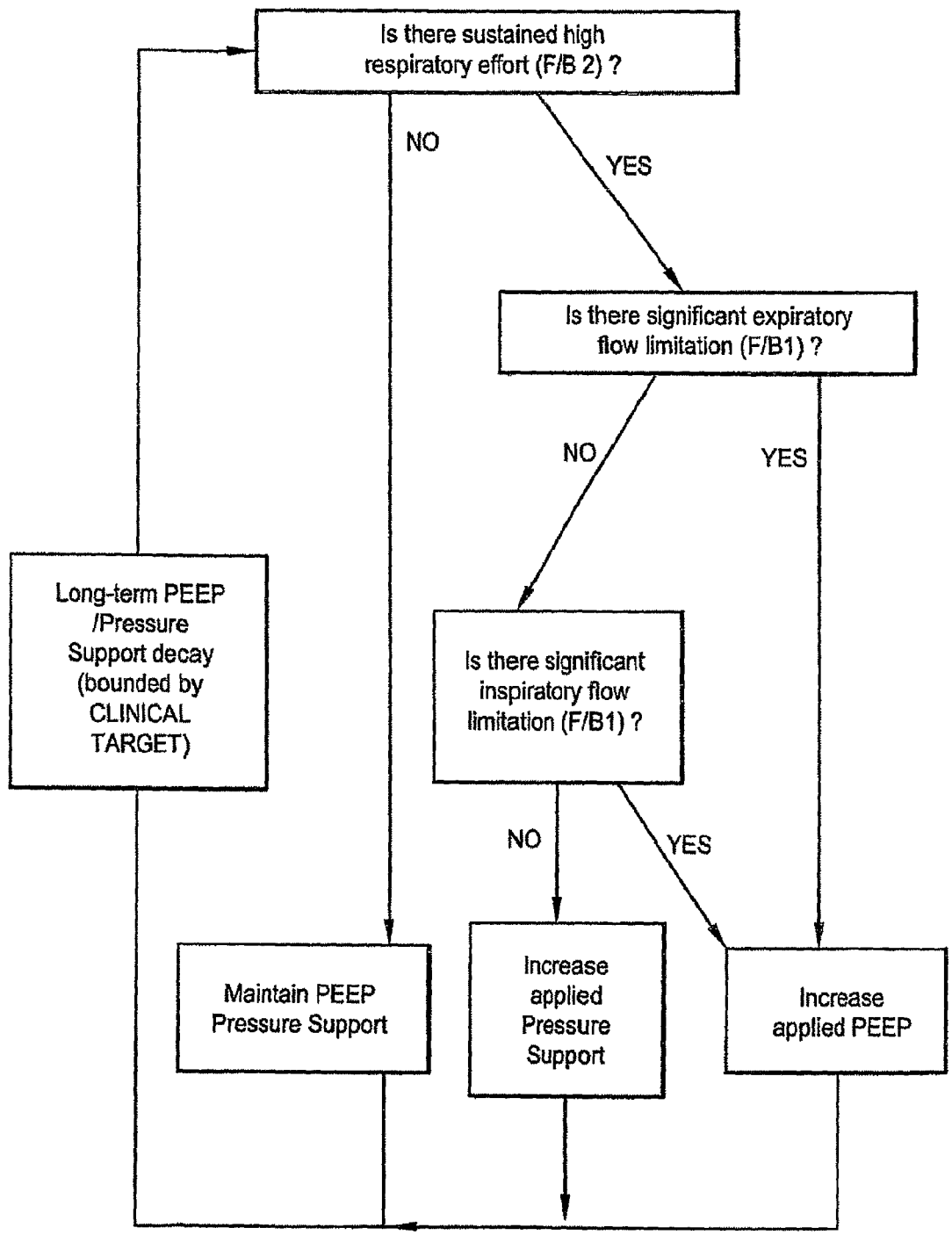
FIG. 5 shows an algorithm for Auto-EEP titration/Automated Pressure Support titration in accordance with an embodiment of the invention.

FIG. 5 shows an algorithm for patients suffering general respiratory insufficiency. The algorithm defines when pressure support, or End Expiratory Pressure (EEP) should be varied.

Figure 6:
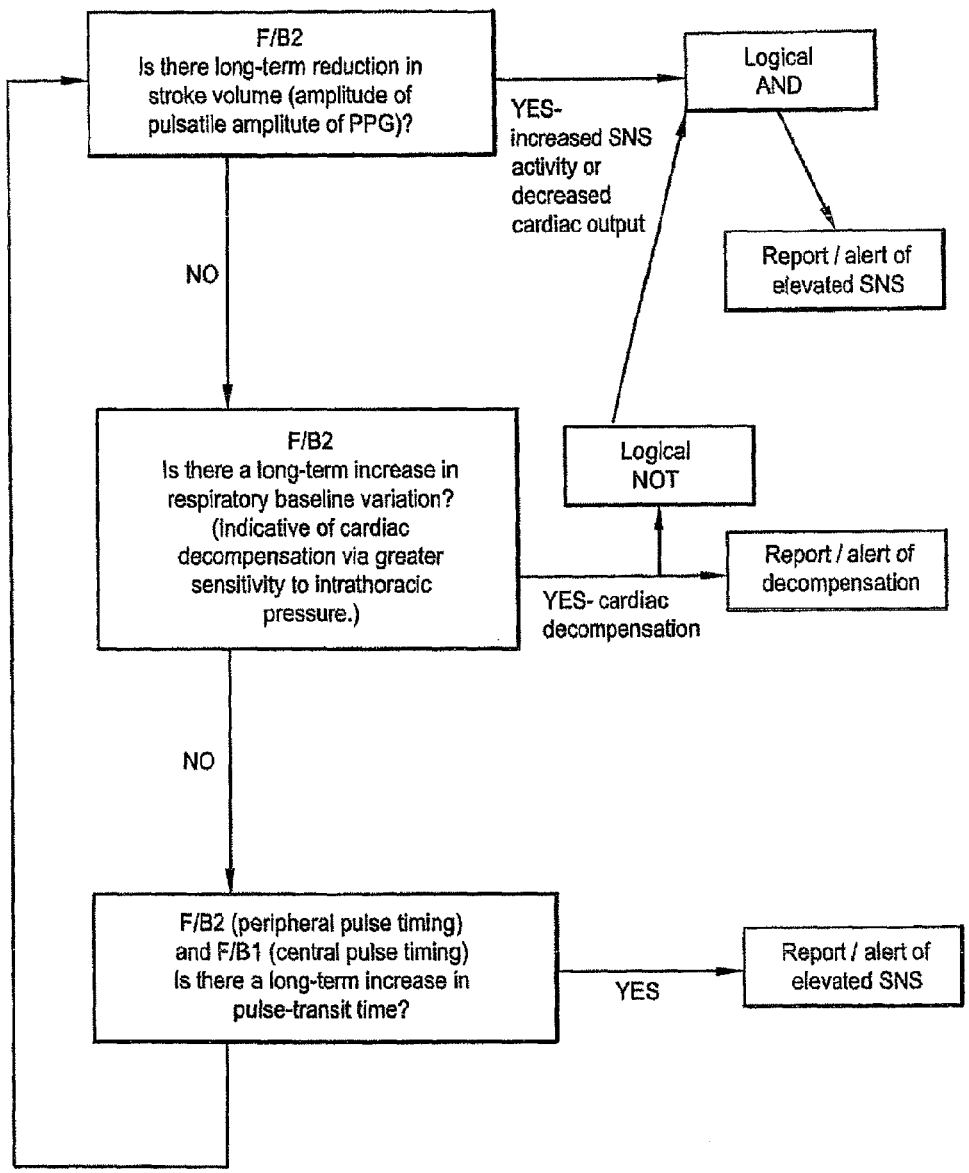
FIG. 6 shows an algorithm for Detection of elevated Sympathetic Nervous System (SNS) or reduced cardiac output—cardiac patients on CPAP/AutoCPAP/Comfort (fixed low-support bilevel) devices in accordance with an embodiment of the invention.

FIG. 6 shows an algorithm which may be part of a monitoring system for evaluating cardiac performance. A cardiac patient may be receiving CPAP therapy and have an additional monitoring device with the algorithm of FIG. 6. Alternatively the CPAP device may incorporate the pulse oximeter. The two signals F/B/1 and F/B/2 are analyzed. Where the values are indicative of elevated levels of SNS activity, or decompensation (poor cardiac performance) an alert is generated. The alert may be in the form of an audible alarm, or part of a messaging system which reports to a physician.

Figure 7:
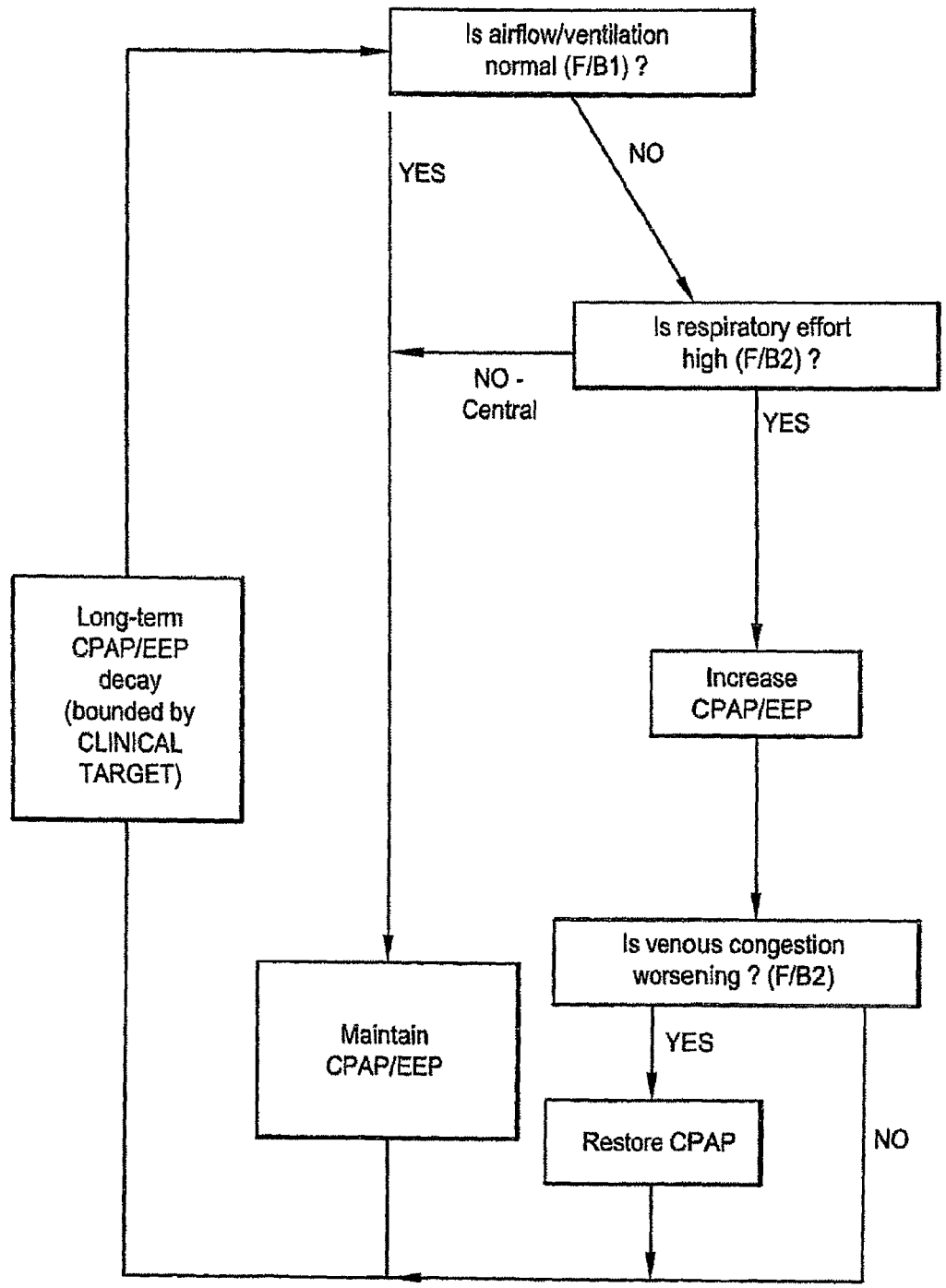
FIG. 7 shows an algorithm for AutoCPAP on cardiac patients in accordance with an embodiment of the invention.

FIG. 7 depicts an algorithm for cardiac patients on CPAP therapy. The algorithm is similar to that in FIG. 4. However, it has the additional step that venous congestion is monitored through the pulse oximeter. If venous congestion is worsening, then CPAP pressure will not be increased, but restored to a previous level.

Figure 8:
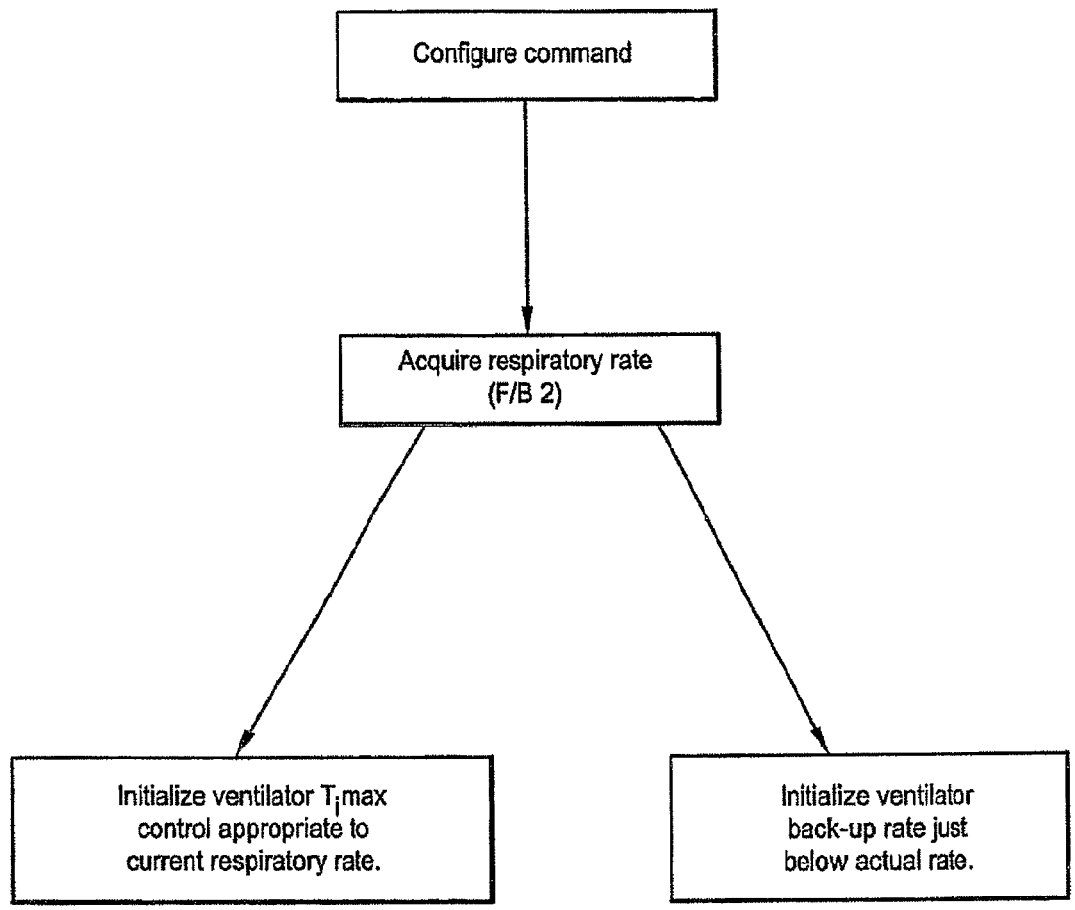
FIG. 8 is a block diagram illustrating a procedure for initializing NPPV therapy rate settings, based on respiratory rate information, in accordance with an embodiment of the present invention.

FIG. 8 depicts a procedure for initializing NPPV therapy rate settings, based on respiratory rate information. Preferably, this is performed after attaching oximeter probe (F/B2), but can be attached prior to commencing ventilation.

Figure 9:
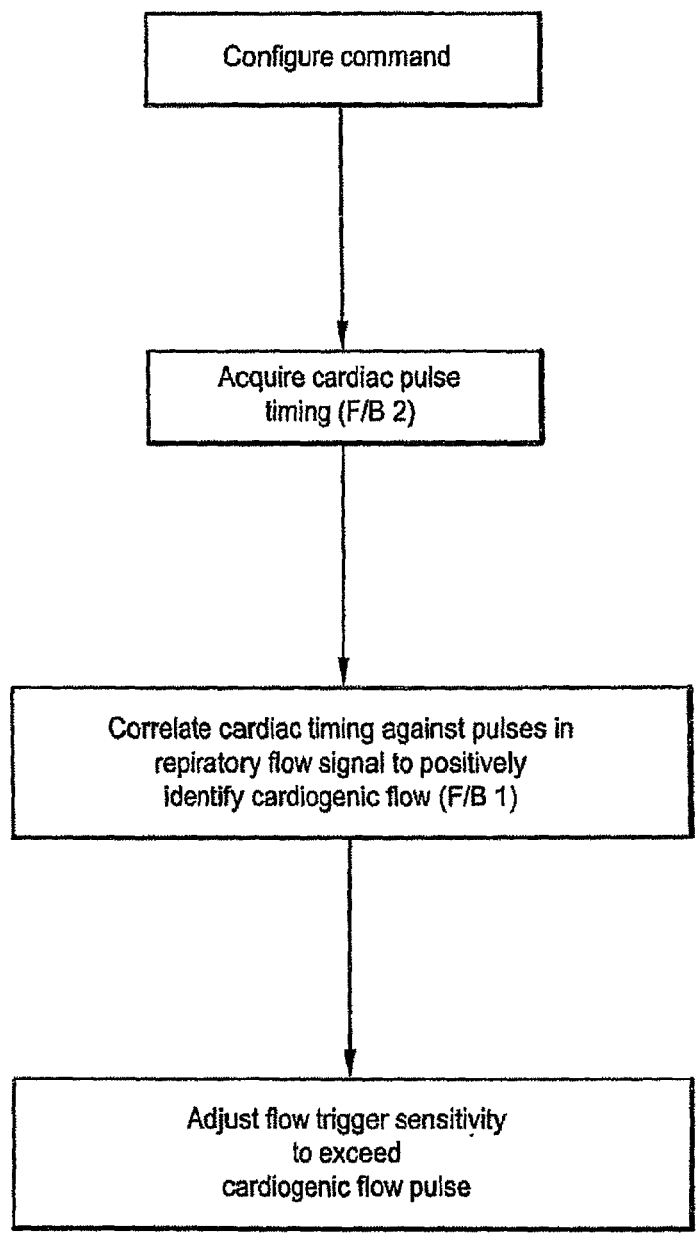
FIG. 9 is a block diagram illustrating a procedure for initializing NPPV therapy trigger threshold settings, based on positively identifying cardiogenic flow amplitude, in accordance with an embodiment of the present invention.

FIG. 9 depicts a procedure for initializing NPPV therapy trigger threshold settings, based on positively identifying cardiogenic flow amplitude. Preferably, this is performed once ventilation is initiated, e.g., so a respiratory flow signal is available.

The combination of traditional oximetry data (saturation, heart rate, pulse timing information) and respiratory timing and effort information (inferred from additional processing of a PPG and/or from the addition of a nasal or oronasal cannulae data) may permit new diagnostic possibilities. For example:

Circulatory delay (delay between breathing changes and saturation changes), an indicator of heart-failure severity or cardiac decompensation.

'True' Pulse Transit Time (PTT), via the delay between cardiogenic flow pulses seen by the nasal pressure transducer at end-expiration (seen at the nares) and the arrival of pulse at the periphery (from the oximeter plethysmogram), as described above.

By extracting respiratory effort information from the raw PPG (pulsus paradoxus) a simple diagnostic system may offer all the key information required for SDB screening except sleep staging: breathing pattern, oxygen saturation, arousal (PTT) or increased systemic vascular resistance, and high effort periods (apnea discrimination and respiratory-effort related arousal (RERA) classification). This system may optionally include a nasal pressure transducer, depending on the relative importance of the derived signals: nasal airflow combined with respiratory effort permits straight-forward discrimination between central and obstructive apneas, but conversely with suitable signal processing, the same information can be gleaned by combining information from the PPG. For example, if increased relative breathing effort precedes oxygen desaturation, an obstructive apnea is discriminated from a central or mixed apnea, in which the desaturation is not accompanied or preceded by increased effort. Similarly, classifier or pattern recognition techniques may be applied to the time course of breathing effort to distinguish obstructive from central apnea.

Other specific examples of where aspects of the invention may be used include:

(a) Using respiratory-related cardiac rhythm variations (e.g., "respiratory sinus arrhythmia") to track and predict breath-phase, and to use the prediction for ventilator triggering. Such variations may conveniently be detected in the PPG, but may also be detected by other cardiac monitoring devices such as ECG electrodes. Typically the respiratory variation imposed on cardiac timing occurs too late to be used as a ventilator trigger: ventilators ideally offer respiratory support coincident with early inspiration, preferably within 100 msec of the patient's initial inspiratory effort. Ventilators typically monitor inspiratory flow or airway pressure variations as a trigger. In severe obstructive respiratory disorders (e.g., COPD) the respiratory flow or pressure information is a poor indicator of inspiratory timing. In such disorders, an alternative 'window' into respiratory activity may offer superior results. Respiration, particularly labored respiration, is known to affect cardiac timing and cardiac output. By monitoring cardiac performance over previous breath cycles, and deriving a respiratory phase signal from cardiac information, the timing of the next inspiratory effort can be predicted, provided the latency of extracting the respiratory signal is not excessive (e.g., more than 1 breath delayed). The central-to-peripheral propagation time for the pulse is typically around 200 msec (the "pulse transit time"), and at best the cardiac cycle would offer a low sample-rate estimate of breath phase (about 4-6 beats per breath). So it is unlikely that a prediction of start of inspiration will not offer precise inspiratory timing. However, such a method still offers significant utility in disease states such as COPD, where ventilator synchronisation via respiratory flow is typically very delayed, and where breath timing may be more entrained than in normal breathing (and therefore predictability being potentially greater).

(b) Using heart-period analysis to infer sleep onset within a sleep-disorder screener device.

(c) A number of measures also can aid in clinical management of home, chronic ventilation, and/or CPAP patients. For example, tracking sleep structure (e.g., start, finish, REM extrapolated from HRV analysis, etc., as described above) within a therapy device can indicate the therapy's effectiveness. Patient-ventilator asynchrony can be extracted from, for example, a PPG spontaneous effort signal. A patient's autonomic improvement in response to therapy (e.g., CPAP) can be measured based on HRV analysis and also can be monitored. An index has been published (Khoo et al., *Cardiac Autonomic Control in Obstructive Sleep Apnea—Efects of Long-term CPAP Therapy*. Am J Respir Crit. Care Med Vol 164. pp 807-812, 2001) that shows a dosage response between CPAP and autonomic nervous activity (e.g., sympathetic and parasympathetic). The index may highlight the benefits of CPAP therapy in minimizing the risk of further adverse vascular events. The index is based on heart-rate variability (originally as acquired by ECG), corrected for the effect of respiratory effort on heart-rate. The PPG signal possesses information on both, so it may by suited to provide this index for long-term trending.

(d) Clinical management and prediction of respiratory exacerbations may be possible, in part, for example, because a pulse oximeter is comfortable and sufficiently easy to use for it to be a routine, long-term home nocturnal monitory. As such, for any chronic respiratory disorder associated with exacerbations that have progressive onset, early detection may be possible if there was a device that could infer relative breathing effort, breathing frequency, breathing phase (including inspiratory and/or expiratory timing). The PPG signal may provide this, and coupled with the inherent arterial oxygenation, may offer a coarse representation of respiratory efficiency (e.g., output vs. input). Applicable conditions may include, for example, asthma, COPD, and the like.

(e) Assessment of endothelial dysfunction: conditions such as respiratory-related arousal during sleep can be considered an involuntary intervention to provoke a sympathetic response. The degree of vasoconstrictive response seen in the PPG acquired from a finger pulse oximeter, trended over a given period (e.g., days, weeks, and/or months), may indicate change in endothelial function, which may be a marker of improving or worsening patient status (e.g., the onset of pre-eclampsia, etc.). The arousal may be entirely spontaneous, or if the patient is on CPAP therapy, can be periodically invoked via a CPAP pressure step-down.

(f) Detection/diagnosis of periodic breathing, (e.g., in cardiac failure patients), evident as periodic variation in the relative respiratory effort signal.

(g) In a ventilator system equipped with customized PPG monitoring, detecting dramatic drop in cardiac output (inferred from PPG amplitude reductions), and asserting an alarm. A drop in cardiac output may be a consequence of many clinically relevant circumstances, e.g., applying excessive positive pressure in a patient with hypovolemia (Yamakage, Can J Anesth 2005 52(2): 207), excessive dynamic hyperinflation/air trapping (Perel, BJA 76(1):168-169) (Conacher, Lancet 1995 346:448).

Advantages for the patient include, for example, more comfort and ease of use. Aspects of the invention provide optimal therapy without being festooned with sensors, e.g., a finger or ear probe is sufficient. Advantages for the physician include, for example, ease to administer. Aspects of the invention provide simple application, automated therapies, and long term patient management feedback. Other advantages include less expensive and improved therapy.

Although the invention has been described with reference to particular embodiments, it is to be understood that these embodiments are merely illustrative of the application of the principles of the invention. Numerous modifications may be made therein and other arrangements may be devised without departing from the spirit and scope of the invention. For example, those skilled in the art recognize that there are other indications of upper airway instability, resistance or obstruction which are not necessarily accompanied by or associated with flow flattening.

Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. An air delivery system, comprising:
a controllable flow generator operable to generate a supply of pressurized breathable gas to be provided to a patient for treatment;
a pulse oximeter configured to generate, during a treatment period, a patient effort signal for input to control operation of the flow generator; and
a controller configured to derive an estimated breath phase of the patient independent of measured flow, based at least in part on the patient effort signal, wherein the controller comprises one or more predictive breath-phase algorithms to improve synchrony based at least in part on the patient effort signal and/or the estimated breath phase and the controller is configured to improve synchrony when inspiratory flow is not an accurate indicator of commencement of inspiratory effort.

2. An air delivery system, comprising:
a controllable flow generator operable to generate a supply of pressurized breathable gas to be provided to a patient for treatment;
a pulse oximeter configured to generate, during a treatment period, a patient effort signal for input to control operation of the flow generator; and
a controller configured to derive an estimated breath phase of the patient independent of measured flow, based at least in part on the patient effort signal,
wherein the pulse oximeter is configured to pre-configure and/or auto-configure one or more of backup rate, minimum machine timing, and maximum inspiratory timing prior to therapy.

3. A method for treating sleep disordered breathing, said method comprising:
deriving a pulse oximeter signal from a patient;
processing the pulse oximeter signal to generate a patient effort signal indicative of respiratory rate;
deriving an estimated breath phase of the patient independent of measured flow based at least in part on the patient effort signal;
analyzing the patient effort signal and/or the estimated breath phase with predictive breath-phase algorithms to improve synchrony; and
improving the synchrony when inspiratory flow is not an accurate indicator of the start of inspiratory effort.

4. A method for treating sleep disordered breathing, said method comprising:
deriving a pulse oximeter signal from a patient;
processing the pulse oximeter signal to generate a patient effort signal indicative of respiratory rate;
deriving an estimated breath phase of the patient independent of measured flow based at least in part on the patient effort signal; and pre-configuring and/or auto-configuring one or more of backup rate, minimum machine timing, and maximum inspiratory timing via a pulse oximeter probe prior to therapy.

5. A respiratory effort monitoring apparatus, comprising:
a pulse oximeter configured to derive a pulse oximeter signal; and
a signal processor configured to receive the pulse oximeter signal and generate a patient effort signal indicative of respiratory rate;
wherein the signal processor is configured to derive an estimated breath phase of the patient independent of measured flow based at least in part on the patient effort signal, and the signal processor is configured to improve synchrony when inspiratory flow is not an accurate indicator of commencement of inspiratory effort.

* * * * *

UNITED STATES PATENT AND TRADEMARK OFFICE
CERTIFICATE OF CORRECTION

PATENT NO.        : 8,646,447 B2
APPLICATION NO. : 12/514696
DATED             : February 11, 2014
INVENTOR(S)       : Martin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1288 days.

Signed and Sealed this

Twenty-ninth Day of September, 2015

Michelle K. Lee
*Director of the United States Patent and Trademark Office*